United States Patent
Tankovich

[19]

[11] Patent Number: 6,063,074
[45] Date of Patent: *May 16, 2000

[54] HAIR REMOVAL USING A CONTAMINANT MATCHED TO A LASER

[75] Inventor: Nikolai Tankovich, San Diego, Calif.

[73] Assignee: ThermoLase Corporation, San Diego, Calif.

[*] Notice: This patent is subject to a terminal disclaimer.

[21] Appl. No.: 08/777,576

[22] Filed: Dec. 31, 1996

Related U.S. Application Data

[60] Continuation of application No. 08/468,022, Jun. 6, 1995, abandoned, which is a division of application No. 08/005,810, Jan. 19, 1993, Pat. No. 5,425,728, which is a continuation-in-part of application No. 07/783,789, Oct. 29, 1991, Pat. No. 5,226,907.

[51] Int. Cl.[7] .................................................. A61B 17/36
[52] U.S. Cl. .............................................. 606/9; 606/133
[58] Field of Search ................................ 606/1, 131, 133, 606/9; 128/898

[56] References Cited

U.S. PATENT DOCUMENTS

| | | |
|---|---|---|
| 3,538,919 | 11/1970 | Mayer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |
| 4,813,412 | 3/1989 | Yamazaki . |
| 5,059,192 | 10/1991 | Zaias . |
| 5,425,728 | 6/1995 | Tankovich ................................ 606/9 |

FOREIGN PATENT DOCUMENTS

| | | |
|---|---|---|
| 1041610 | 6/1974 | Canada . |
| 1208702 | 7/1986 | Canada . |
| 2267122 | 4/1975 | France . |
| 2595239 | 6/1982 | France . |
| 2590791 | 6/1987 | France . |
| 2515697 | 10/1975 | Germany . |
| 32209G2 | 6/1982 | Germany . |
| 8002640 | 12/1980 | WIPO . |
| 8602783 | 5/1986 | WIPO . |
| 9104073 | 4/1991 | WIPO . |

OTHER PUBLICATIONS

Porphyrins in Tumor Phototherapy —Andereoni 1984—pp. 143–155.

Investigation and Therapy in Dermatology A. Anders, et al—Conf. Laser 77 Optics–Electronics Jun. 20–24, 1977).

*Primary Examiner*—Glenn K. Dawson
*Attorney, Agent, or Firm*—Fish & Richardson P.C.

[57] ABSTRACT

A device and process for the permanent removal of unwanted human hair. Hair on a section of skin is contaminated with a substance having high absorption of a frequency band of light. The skin is illuminated with light at this frequency band at sufficient intensity and duration to kill the follicles or the skin tissue feeding the hair. One embodiment to produce death of the follicles or the skin tissues feeding the hair is by photochemical reaction.

20 Claims, 5 Drawing Sheets

HAIR REMOVAL USING A CONTAMINANT MATCHED TO A LASER

This is a file wrapper continuation of Ser. No. 08/468,022, filed Jun. 6, 1995 and now abandoned, which was a division of Ser. No. 08/005,810, filed Jan. 19, 1993 and now U.S. Pat. No. 5,425,728, which was a continuation-in-part of Ser. No. 07/783,789, filed Oct. 21, 1991 and now Pat. No. 5,226,907.

BACKGROUND OF THE INVENTION

The principal methods presently used for hair removal involve the use of electrolysis techniques or chemical depilatories. These techniques involve some pain, are time consuming. and demand a fair degree of expertise in their application and normally do not guarantee a permanent effect.

Laser use in medicine is well known. For example, lasers are used in surgery for both cutting and cauterization. Lasers have been used for many years for removing tattoos under the surface of the skin. In this case a laser beam penetrates the skin and is absorbed by and destroys the ink particle. A similar procedure has been used for years to remove birth marks where the laser is matched to an absorption peak of the erythrocyte's hemoglobin in the tiny capillaries under the skin to destroy the capillaries.

The prior art of hair removal also includes attempts at removing hair with laser beams. Three such techniques are described in the following United States patents: Weissman et al. Method for Laser Depilation Device and Method, U.S. Pat. No. 4, 388,924; Sutton, Depilation Device and Method, U.S. Pat. No. 4,617,926; and Mayer, Depilation by Means of Laser Energy. U.S. Pat. No. 3,538,919. All of these devices and methods teach the removal of hairs one hair at a time with a narrowly focused laser beam. Therefore, they are relatively inefficient and time consuming. A recent patent by Zaias, U.S. Pat. No. 5,059,192 issued Oct. 22, 1991 discloses a process for using a laser beam matched to the melanin found at the base of the hair follicle and papilla.

It has been known for at least 20 years in the medical profession that selective absorption of laser radiation can sometimes be enhanced by the technique of staining pathological tissues with various vital dyes. (See Goldman U.S. Pat. No. 3,769,963.)

What is needed is a simple, harmless device and method for removal of hair over a relatively broad area of skin.

SUMMARY OF THE INVENTION

Present invention provides a device and process for the permanent removal of unwanted human hair. The hair or the skin tissue feeding or surrounding the hair on a section of skin is contaminated with a substance having high absorption of a frequency band of light. The section of skin is illuminated with light at this frequency band at sufficient intensity and duration to kill the follicle or the skin tissue feeding the hair. Specific embodiments produce death of the follicle or the tissue by photochemical reaction.

DETAILED DESCRIPTION OF PREFERRED EMBODIMENTS

Preferred embodiments of the present invention can be described by reference to the figures.

COAT AND HEAT METHOD

Skin Preparation

Figure 1:
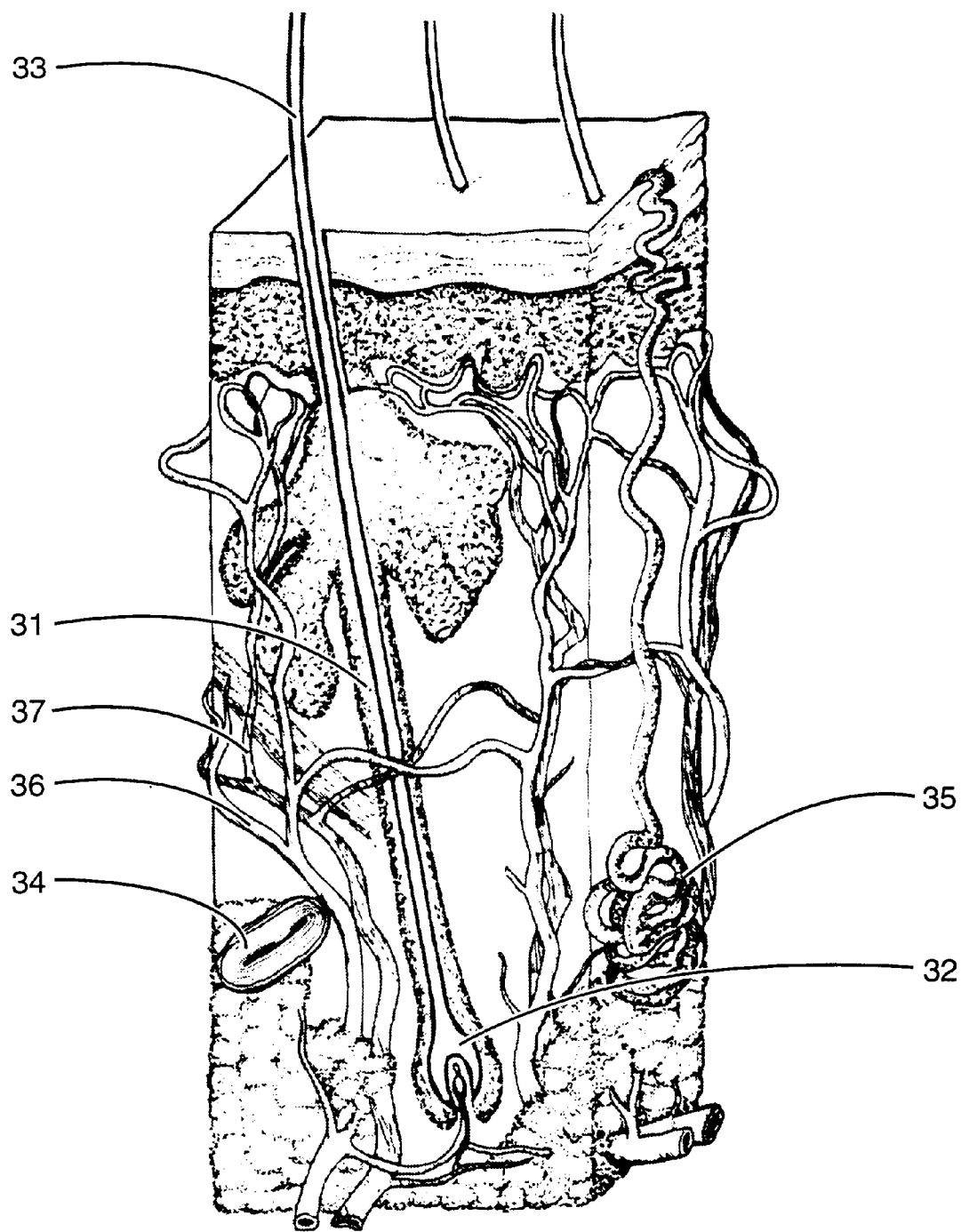
FIG. 1 is a drawing of a section of human skin showing a growing hair.

A section of human skin showing a cross section of one hair is shown in FIG. 1. A first preferred embodiment of the present invention can be described by reference to FIGS. 2–4. FIG. 1 shows the hair shaft 33, a nerve ending 34, a sweat gland 35 and arteries 36 and veins 37. First, a laser absorbing carbon suspension is prepared of carbon powder in peach oil. The particle size of the powder preferably is about 10–20 nm and its concentration preferably is about 15% to 20% by volume.

Figure 2A:
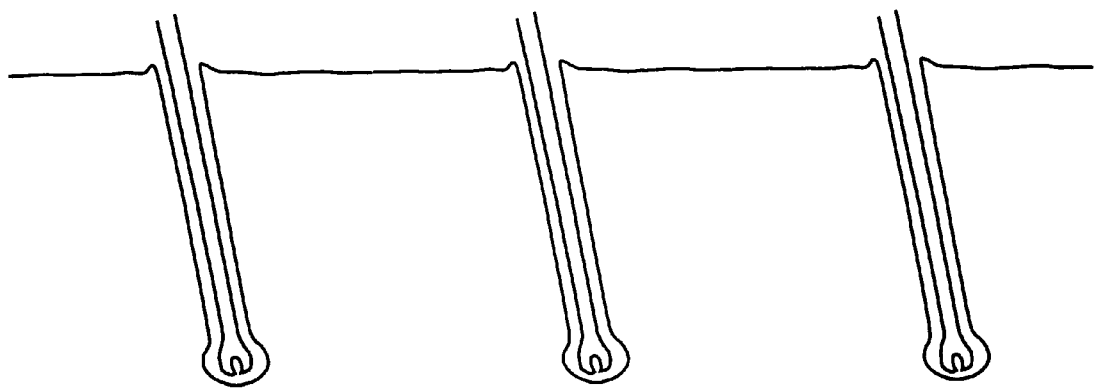
FIGS. 2A, B and C show a cross section of skin and 3 hairs during 3 stages of a process of one embodiment of the present invention.
Figure 2B:
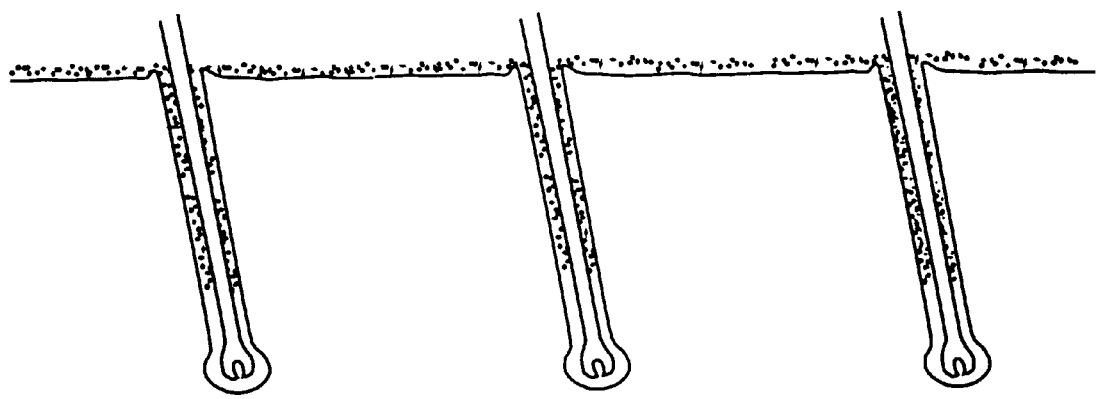
Figure 2C:
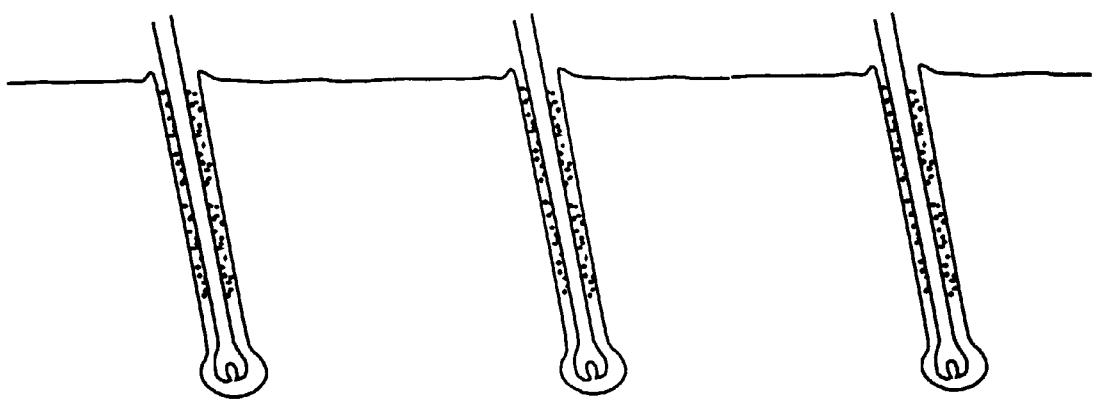

A clean section of skin is depicted in FIG. 2A. This suspension is rubbed on the skin with a massaging action so that portions of the carbon suspension infiltrates the hair ducts of the hair that is to be removed as shown in FIG. 2B. Ultrasound with frequencies in the range of 3.5 to 10 MHz at a power level of about 0.1 to 0.2 with 4 to 5 minutes could be used to help force the suspension into the ducts. Next the surface of the skin is cleaned preferably with an alcohol pad to make the skin surface clean but to leave the hair pores contaminated with the carbon suspension as shown in FIG. 2C.

Laser Application

The laser device used in this preferred embodiment is a $CO_2$ pulse laser which has the spikes in the range of 10.6 microns. Light in this range will pass through the outer layer of the surface of the skin and is readily absorbed in carbon. Laser parameters such as pulse width repetition rate can be selected to best fit the skin and hair types of the patients. The parameter for two specific examples which I have utilized with good results for hair removal are shown in Table 1:

TABLE 1

Parameters Preferred.

| | First Example | Second Example |
|---|---|---|
| Pulse Width | 275 ns | 200 ns |
| Repetition Rate | 30 Hz | 8 Hz |
| Laser Spot Size | 1 cm$^2$ | 1 cm$^2$ |
| Energy per pulse | 0.1 Joule | 0.2 Joule |
| Scanning Rate | 20 seconds per 10 cm$^2$ | 30 seconds per 10 cm$^2$ |

Each point on the skin receives illumination for about 2 seconds and each square centimeter receives about 6 Joules. Some of the light is reflected. Of the light which is not reflected a significant portion of the energy of each pulse is absorbed in the carbon.

Figure 3:
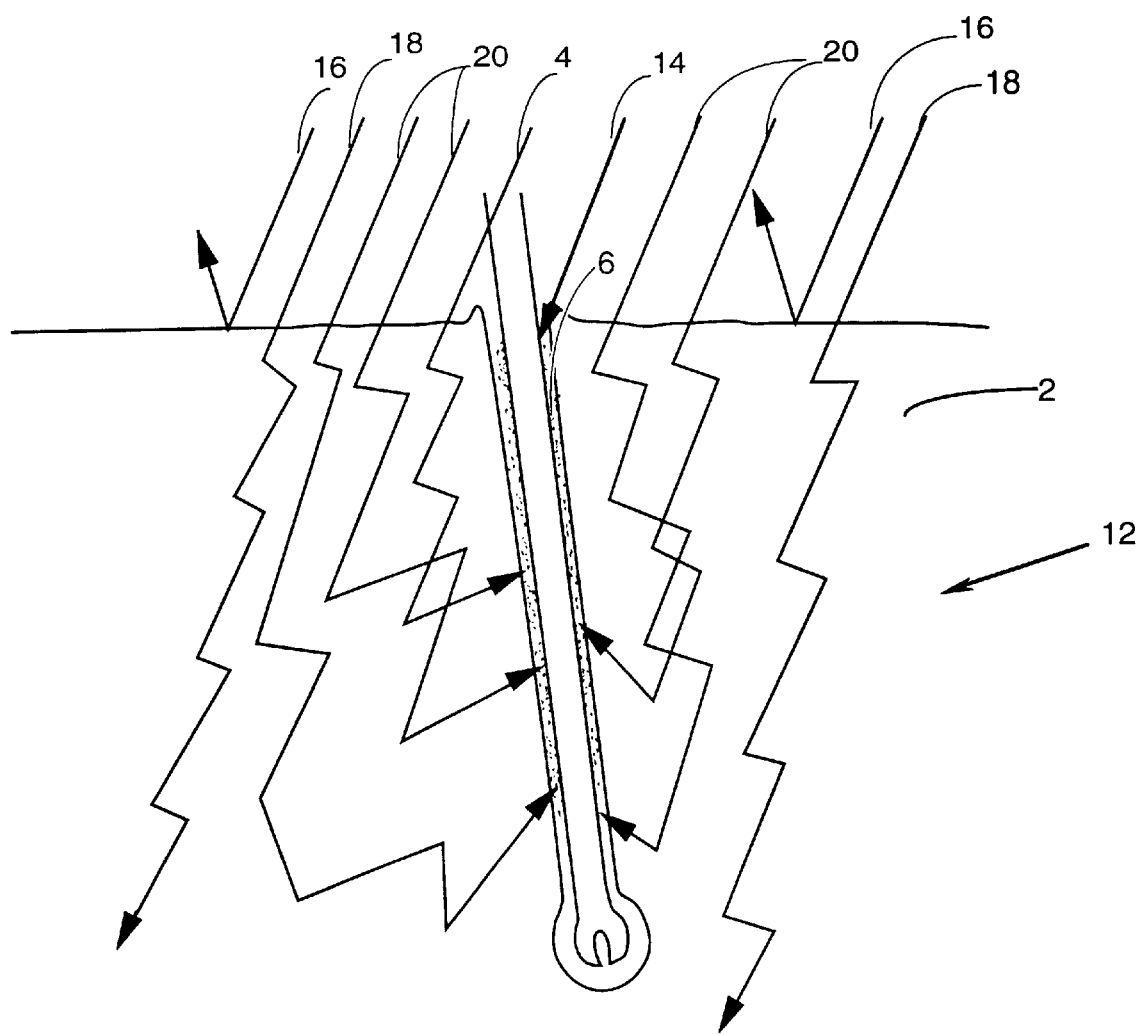
FIG. 3 shows qualitatively the paths of the photons of a laser pulse showing absorption in a carbon-oil suspension.

FIG. 3 shows a simplified view of a section of human skin and qualitatively the paths 12 of some of the photons of a laser pulse illuminating a section of skin 2 containing a hair duct with a hair 4 contaminated with carbon suspension 6. A few of the photons travel directly through the skin and are absorbed in the carbon (depicted by photon 14). Some are reflected from the skin surface (depicted by photons 16). Some are absorbed in the skin (depicted as photons 18) and a portion of the photons are absorbed in the carbon.

Operating within the parameters specified is important. They have been chosen to preferentially heat the carbon suspension which in turn heats the hair follicles and the blood vessels feeding the follicles to temperatures high enough to kill the hair follicles and/or the tissue feeding the follicles but to minimize the heat to the rest of the skin tissue. The energy application time is a most important parameter. It must be chosen so that a large amount of energy is deposited in the suspension quickly so that the temperature of the suspension rises rapidly to about above 70–80° C. This temperature applied for about 1 second is high enough to kill the follicles and/or the vessels feeding the follicles. During this short period heat transferred to the skin tissue is not enough to damage the skin tissue except that tissue immediately surrounding the follicle. A good practice is to start out with the power densities specified. It will be evident when enough energy is being supplied because the hair shaft will begin to curl. If curling is not achieved the power density could be increased up to about 2–3 Joules per square centimeter or until sufficient energy is delivered to deutilize the hair.

I have performed hair removal experiments using the parameters shown in Table 2 with excellent results. There is no significant pain. The hair is permanently removed and there is no apparent detrimental effect.

I performed a qualitative mathematical analysis in order to estimate heat absorption and temperature distribution in the hair and skin tissue. This analysis is shown in Table 3.

Thus, under these assumptions each pulse would heat the carbon oil suspension roughly about 5° C. (The reader is cautioned that the above analysis is not to be relied on as a quantitative description of the process of heating the carbon oil suspension in the hair duct. For example, for many people the assumption that ¼ of the energy of each pulse goes into the hair duct is probably too high.)

Each pulse will also heat the skin in general. I do not have a good estimate of the portions of the energy of the pulse reflected, absorbed in the hair ducts and absorbed in the skin in general. However, we have assumed for this qualitative analysis that about ½ of the energy the laser pulse reflects, ¼ is absorbed in the hair ducts and ¼ is absorbed in the skin in general. If we assume that the skin is heated fairly uniformly to a depth of 0.2 cm, a skin density of 1 gm/cm³ and a specific heat for the skin, of 4 J/gm ° C. the 0.025 J pulse will heat this typical skin section

TABLE 2

Heating of hair and carbon oil suspension in hair duct.

| | |
|---|---|
| Repetition Rate | 33 pulses per second |
| Time between pulses | about 0.03 seconds |
| Hair duct diameter | 0.1 mm |
| Energy per Pulse | 0.1 J |
| Energy per second | (0.1 J) (33) = 33 J/sec = 3 W |
| Beam spot | 1 cm² |
| Hair spacing | 130 hairs/cm² |
| Distance between hairs | 0.1 cm = 1 mm |
| Assume ¼ of energy goes into hair duct | |
| Energy per hair per pulse | (0.1 J/130)/4 = 0.00016 J |
| Volume of hair duct | |
| Length 1 mm | |
| Diameter 0.1 mm | |

TABLE 2-continued

Heating of hair and carbon oil suspension in hair duct.

| | |
|---|---|
| $\text{Vol.} = l\pi\left(\dfrac{D}{2}\right)^2 =$ | $(0.1 \text{ cm})\pi\left(\dfrac{0.01}{2}\right)^2 = 0.0000078 \text{ cm}^3$ |
| Density of oil and hair = | 0.9 gm/cm³ |
| Mass of oil & hair | 0.000007 gm |
| Specific heat of oil & hair assume | 4 J/gm ° C. |
| Temperature rise per pulse, $\Delta T = \dfrac{Q}{mc}$ | $\dfrac{0.00016 \text{ J}}{(0.000007 \text{ gm}) 4 \text{ J/gm } °\text{C.}} \approx 5° \text{ C.}$ | about 0.04 degrees C. Based on these assumptions, the 60 pulses over about 2 seconds will give a general heating of about 2° C. Therefore, heat deposited generally to the skin would be negligible. (Again, the reader is cautioned regarding the qualitative nature of this analysis. In practice I believe much of the energy from the pulse $CO_2$ laser is absorbed in a very thin area of the surface possibly as thin as 0.1 mm depending on the dryness of the skin. In some cases a very thin layer of the skin is actually vaporized in the process, but this is usually the layer which consists of essentially dead cells which naturally flake off the skin surface. Also, since the epidermis is such a poor heat conductor the underlying layers of skin is typically protected from damaged except those portions very close to the carbon oil suspension.)

However, heat from the hot carbon oil suspension will be transferred by conduction to the tissue surrounding the hair duct. I used the following relationship (see note 10 of Zwig & Wibber, IEEE Journal of Quantum Electronics, Vol. QE-23, No. 10 October (1987), Mechanical and Thermal Parameters In Pulsed Laser Cutting of Tissue) to estimate the heat spread from the hot carbon oil suspension in the duct:

$$\delta = \sqrt{K\tau}$$

where $\delta$ represents the thickness of a heated zone during a time $\tau$, K being the heat of conduction. Assuming K=1.44× $10^{-3}$ cm²/S and using 0.03 sec as the time interval between pulses, we estimate that the heat spreads out by about 0.007 cm from the hair duct between each pulse. This is about equal to the radius of the hair duct so we assume that about one half of the temperature rise from each pulse is transferred to the surrounding tissue during the 0.03 second following each pulse. This means that the net increase in the temperature of the carbon-oil suspension from each pulse will be roughly 2.5° C.

Figure 4A:
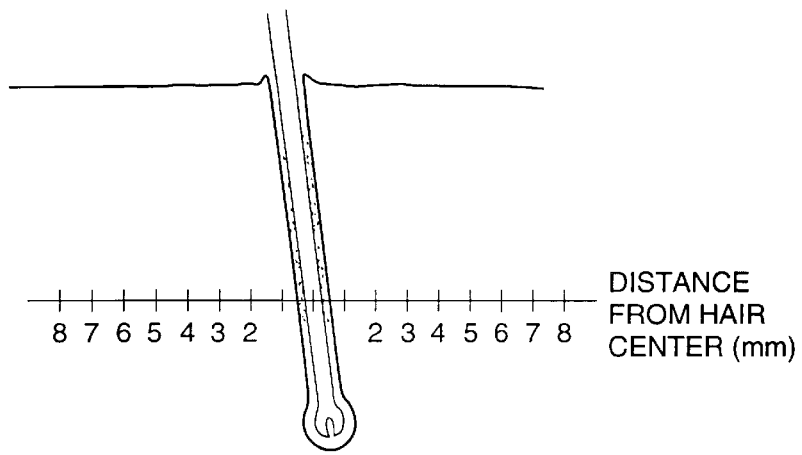
FIG. 4A and B show the temperature distribution near a typical hair during the process of a preferred embodiment of the present invention.
Figure 4B:
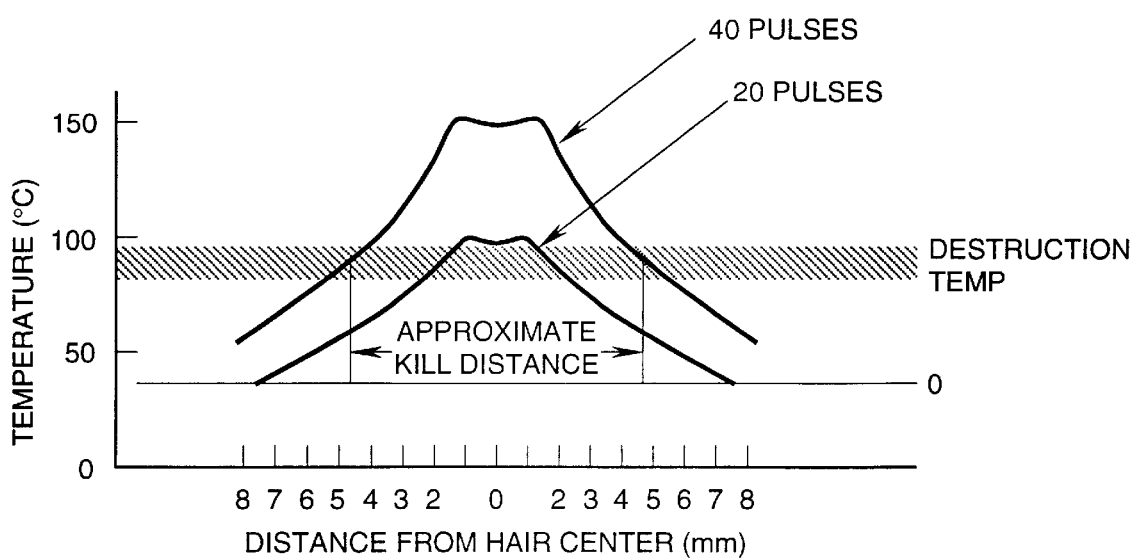

Thus, as depicted in FIG. 4 in about ⅔ second the temperature of the carbon-oil suspension in the hair duct has risen from a normal temperature of 37° C. to about 90° C., a temperature high enough to kill the follicle and the tissue cells immediately surrounding the hair follicle (i.e., within about ±5 hair diameter). In a little more than one second the temperature has risen to about 140° C. which I currently propose as the upper range. At this point the patient would begin to feel pain. Therefore, the illumination should be applied so that no spot is illuminated longer than about one or two seconds during one scan. FIGS. 4A and 4B shows a rough approximation of the temperature distribution between ±8 millimeters of the center for a typical hair duct after 20 and 40 pulses.

For this process I illuminate a 10 cm² area by making 2 or 3 passes over each spot during a 20 second scanning period. For each spot the temperature will have dropped from the range of about 100° C.–140° C. to below about 50° C. during the approximately 7 seconds between scans.

As a result of the illumination, I estimate that for many patients essentially all follicles will be killed or will die within 2 weeks because of reduced nourishment due to the destruction of the tissue surrounding the hair duct which feed the follicle. I also estimate that the destroyed tissue is confined to within about 3–6, millimeters (about 6–12 hair diameters) of the center of the hair. Although I list this as a preferred embodiment, it does not work well on all persons. In some cases pain and some surface burning is experienced before the hair tissue is destroyed. For these persons, one of my alternative embodiments is recommended.

NEAR INFRARED LASER METHOD

This process is the same as the first embodiment described above except the laser wavelength is 1.06 microns, the pulse duration is about 1000 times less (i.e, in the range of 25–30 pico seconds), the energy per pulse is about 100 times less or about 3–6 mJ and the spot size is about 0.1 to 0.3 cm$^2$. At this wavelength the skin penetration is maximum. In this case much less energy is required because a much larger percentage of the energy is absorbed in the contaminant.

STAIN METHOD

Figure 5:
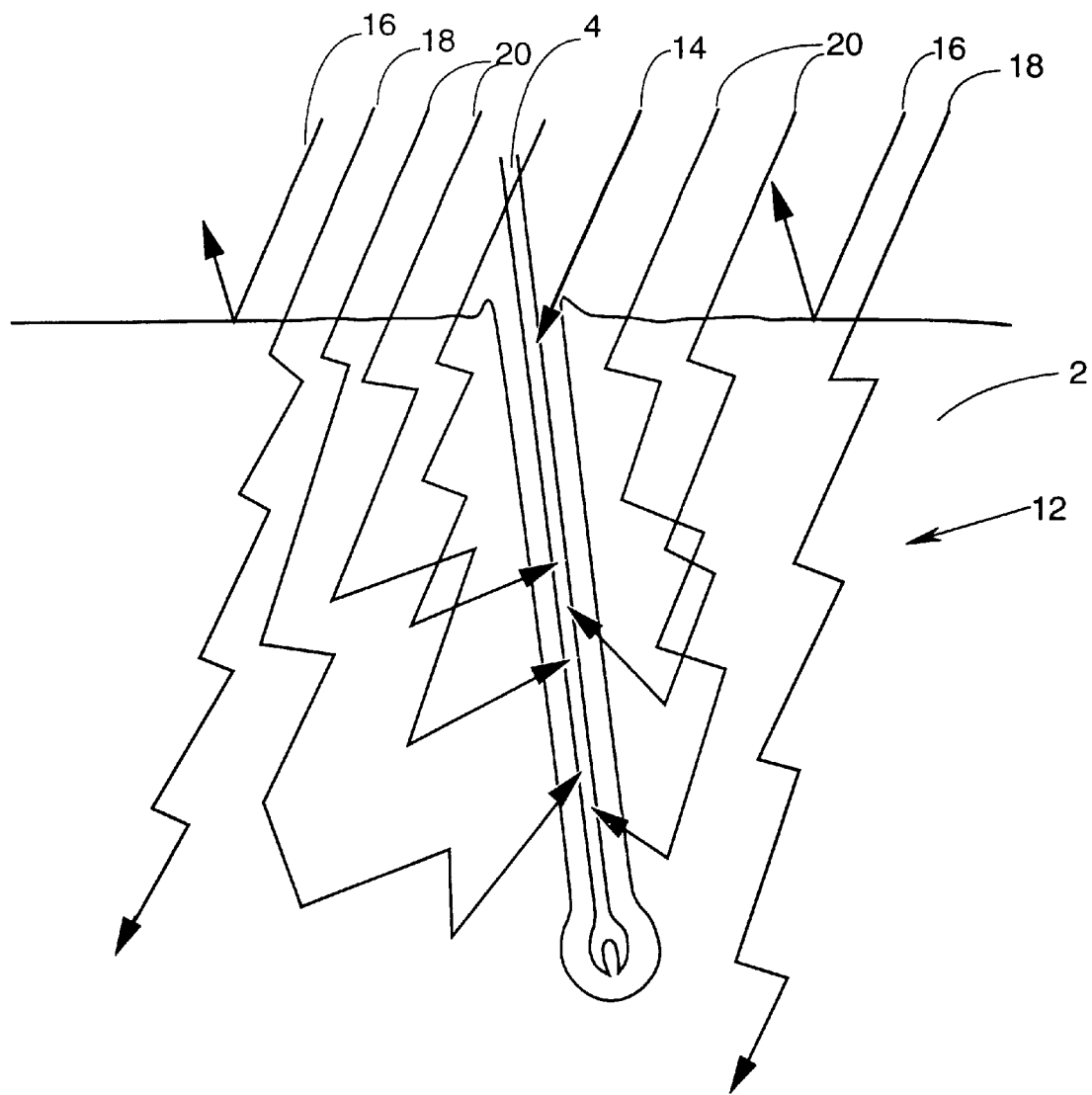
FIG. 5 shows qualitatively the paths of the photons of a laser pulse showing absorption in hair dye.

A second embodiment involves the use of dyes to stain the hair follicles. A pulse laser beam of light having a wavelength corresponding precisely to a resonance frequency of the dye illuminates the hair and skin area where the hair is to be removed. The dye and laser beam are chosen so that there is very little absorption by the skin tissue but great absorption by the dye. As indicated in FIG. 5 the photons will undergo diffuse reflection in the skin. But when a photon intersects the hair it is absorbed.

To stain the follicles, dye is mixed to form a solution which will penetrate into the follicles. A good substance used to form this solution is hydropertis. In one embodiment. I use commercial hair dye #124 (deep black with blue) and India ink which already contains such a solution. It is rubbed on the skin and hair and let stand for 30 minutes. The dye will migrate through the hair all the way to the root. India ink could also be used.

The skin is cleaned using standard dye removal solution. This India ink and dye #124 have an absorption peaks at ~694 nm and ~587 nm which matches perfectly with the wavelength of 587 nm dye laser. Dye #124 also has a resonance of 531 and 584 nm corresponding to the output of a copper vapor laser supplied by Spectra Physics.

For this embodiment I use a pulse width of 150 ns ruby laser and 200 μs dye laser. With a beam cross section diameter of 0.4 cm, the energy density is 2.5–8.5 J/cm$^2$. There are many other dye-laser combinations available which will be obvious to persons skilled in the laser art. The secret is to match the laser wavelength with a resonance peak in a dye which can be applied to and absorbed in the follicles. Inida ink (essentially the same as tattoo ink) has a high absorption from UV up to 1 R.

I have described below a good general procedure for hair removal practicing the stain method.

1. Discolor hairs with hydroperoxide 1 hour prior to staining hairs.
2. Cut or shave hairs leaving about 1 mm of hair above the skin.
3. Stain hairs with the ink or dye (red or orange, preferably). More ink or dye would be located around the hair and its pores because of the liquid surface tension near the hair.
4. Leave substance covered for 40–50 minutes.
5. Wash skin surface several times with alcohol, until the skin surface returns to its normal color, except hair pores.
6. Make 3–4 spots for the test with different power densities to choose individual optimal dose for the patient.
7. Start lasering in 3–6 hours after the staining procedure, one laser shot per spot.
8. Cover the area irradiated with Aloe Vera Gel or Laser Cream after the procedure.
9. Give these instructions to the patient:
   use Bicicytrine ointment topically first three days;
   spare the area irradiated when taking shower, don't use hard sponges;
   protect the area from direct sunlight by sunscreen or dress:
   take Tylenol if there is any discomfort;
   call if necessary.
10. Examine the skin in 1, 2 and 3 weeks.
11. Repeat the procedure if necessary for the hairs which were in Anagen or Catagen phases during the laser HR.

Titanium-Sapphire laser could be used. This laser covers the parameters of Ruby laser, penetrates human skin about as well as the Ruby laser and has a wider band of radiation within the absorption spectrum of these dyes.

PHOTO CHEMICAL DESTRUCTION

A third embodiment for practicing this invention is to apply a photosensitizes to the hair so that it is absorbed along the full length of the hair to the root. The skin area is then illuminated with laser light which readily penetrates the skin but is absorbed resonantly by the photosensitizer. The photosensitizer undergoes a chemical reaction which is deadly to the hair follicles.

A good specific example of this embodiment of the present invention is to apply a 20% solution of hermotoporphin derivatives topically to the skin over where the hair to be removed has been recently shaved. The solution is absorbed into the portion of the hair remaining under the skin by capillary action. The skin is then cleaned thoroughly with an alcohol pad. Next the skin area is illuminated with an argon dye laser at 632 nm. The energy required is about 5–10 Joules per square centimeter. In this case, the time period is not very important. It could be several minutes per square when the laser energy is absorbed in the hermotoporphin derivatives, singlet oxygen is produced as a result of photochemical reaction. The singlet oxygen is toxic for protein and phosphorlipids in the hair follicles and the follicles are thus killed.

SKIN COVER METHOD

This method is essentially the same as the Coat and Heat Method described above except that the surface of the skin is not cleaned after the application of and massaging in of the carbon-oil suspension. The skin surface appears like that shown in cross-section in FIG. 2B instead of 2C for the irradiation step. In this case the carbon-oil suspension serves as a shield for the skin surface permitting higher laser doses with no significant injury to the epidermis and dermis of the skin. Preliminary tests indicate that this is a very effective and safe method of hair removal. The outermost surface of the skin being a very good insulator prevents any substantial heat transfers to the lower layers of the skin and prevents any significant damage to the skin.

ORAL AND INTRAVENOUS CONTAMINATION OF HAIR OF TISSUE

It is also possible to contaminate orally or intravenously the hair or tissue feeding the hair. A preferred method for oral contamination is as follows:

A solution of disodium fluoresein 2–5% consentration given orally. Within 3 to 72 hours a significant portion of the disodium fluoresein will be concentrated in the body hair of the patient. Sections of the skin containing the hair to be removed is irradiated with a laser pulsed at a wavelength matched to NaFl. Preferred laser sources are HeCd (441 nm), Nd:YAG (1,064 nm) frequency shifted to about 532 nm and Er:Glass (1.54 $\mu$s) tripled to 513 nm. Other sources with wavelengths from 370 nm to 520 nm would be satisfactory. Preferred power levels are between 5 to 15 J/cm$^2$ depending on hair depth, type of skin Disodium Fluoresein metabolism, etc. Preferred pulse duration is 1 $\mu$s or less.

OTHER CONTAMINANT—LASER COMBINATIONS

There are many other chemicals which can be used in the stain method and the photochemical method. I have listed in Table 3 some of these along with a corresponding recommended laser for the illumination.

OTHER EMBODIMENTS

It is very important for all of these embodiments and in other embodiments which will be apparent to persons skilled in the art that the light absorbing substances have a very high absorption coefficient at frequencies which pass readily through the surface of the human skin. An illumination source is matched to this frequency. The substance used can be one with a high resonance peak at the frequency or it can be one with a high broad absorption coefficient over a wide band continuing the illumination frequency. The important thing is to use a light of a frequency which defuses through the skin and has a relatively low absorption in the skin and to use an absorber for contaminating the hair which will provide very high absorption of the light. Persons skilled in the art will recognize that certain frequencies will be preferred for light skinned persons and other frequencies may be preferred for dark skinned persons. The preferred beam size is about 1 square centimeter but could be as large as about 5 square centimeters.

TABLE 3

Dyes and matching laser.

| DYE | LASER |
|---|---|
| Hematoporphyrin derivatives | Argon Dye (630 nm) |
| Indocyanine Green | Diode Laser (785 nm) |
| Microcyanine | Cooper Vapor (540) |
| Photophrin II | Argon Dye (630) |
| Chlorin - E6 | Dye (660) |
| Chlorophyll derivatives | Argon Dye (630) |
| Black Ink | Ruby Laser (694) |
| Any of the above dyes | Tunable titanium-sapphire |

While the above description contains many specifications, the reader should not construe these as limitations on the scope of the invention, buy merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

I claim:

1. A process for inhibiting growth in a section of human skin, of a plurality of hairs growing in hair ducts from follicles at the bottom of said ducts and nourished by skin tissue immediately surrounding said follicles, essentially without damage to skin tissue except to said skin tissue immediately surrounding said hair ducts, the space inside each of said ducts not occupied by one of said hairs defining a hair duct, said process comprising the steps of:

a. selecting a contaminant having optical absorption of at least one frequency band of light which will penetrate said section of skin, b. applying said contaminant topically to said section of skin in such a manner as to cause a portion of said contaminant to infiltrate the duct spaces in said hair ducts, and c. illuminating said section of skin with said at least one frequency band of light, a significant portion of which penetrates the section of skin and is absorbed in said contaminant in said hair ducts, causing a reaction which heats said follicles and/or the skin tissue feeding said follicles so as to inhibit hair growth.

2. The process as in claim 1 wherein said at least one frequency band of light is produced by an Nd:YAG laser.

3. The process as in claim 2 wherein said contaminant comprises particles suspended in a medium.

4. The process as in claim 3 wherein said particles have a size of about 10 nm to about 20 nm.

5. The process as in claim 3 wherein the particles comprise graphite particles.

6. The process as in claim 5 wherein the contaminant is heated to a temperature of about 70° C. to about 80° C., and the reaction transfers heat from the contaminant to skin tissue immediately surrounding said hair ducts so as to cause removal of said hairs.

7. The process as in claim 6 wherein the temperature of the contaminant rises to about 70° C. to about 80° C. for about 1 second and the hair on the section of skin begins to curl.

8. The process as in claim 2 wherein the frequency band of light comprises light having a wavelength of about 1.06 micron.

9. The process as in claim 2 wherein the laser produces pulses of said light having a duration in the range of about 25 to about 30 pico seconds.

10. The process as in claim 9 wherein the energy of each of the pulses is about 3 mJ to about 6 mJ.

11. The process as in claim 10 wherein the laser produces a beam having a spot size of about 0.1 to about 0.3 cm$^2$.

12. The process as in claim 1 wherein said at least one frequency band of light is produced in a series of pulses by a pulse laser.

13. The process as in claim 12 wherein another portion of said contaminant remains on the surface of said skin section and is vaporized by one or more of the pulses in said series of pulses so as to permit subsequent pulses in said series of pulses to penetrate said skin section and be absorbed in said contaminant in said hair ducts.

14. The process as in claim 1, wherein said illuminating step is carried out while observing the section of skin undergoing illumination, hair being present on said section of skin, and continuing said illuminating at least until the hair on the section of skin begins to curl.

15. The process as in claim 1 wherein said at least one frequency band of light is produced by a $CO_2$ laser and the at least one frequency band of light is about 10.6 microns.

16. The process as in claim 15 wherein said laser produces pulses of said light defining a pulse duration of about 200 nanoseconds to about 275 nanoseconds.

17. The process as in claim 16 wherein said pulses have a frequency of about 8 to about 30 Hz.

18. The process as in claim 16 wherein the pulses have an energy of about 0.1 J to about 0.2 J per pulse.

19. The process as in claim 15 wherein said laser produces a beam of said light having a spot size of about 1 $cm^2$.

20. The process as in claim 19 wherein the beam of the laser is scanned over the section of human skin at a rate of about 20 to about 30 seconds per 10 $cm^2$.

\* \* \* \* \*

UNITED STATES PATENT AND TRADEMARK OFFICE
CERTIFICATE OF CORRECTION

PATENT NO.    : 6,063,074
DATED         : MAY 16, 2000
INVENTOR(S)   : NIKOLAI TANKOVICH

It is certified that error appears in the above-identified patent and that said Letters Patent is hereby corrected as shown below:

Column 5, Line 38, Delete period "." in "In one embodiment. I use" and insert - -","- -.

Signed and Sealed this

Seventeenth Day of April, 2001

*Attest:*

NICHOLAS P. GODICI

*Attesting Officer*    *Acting Director of the United States Patent and Trademark Office*